United States Patent [19]

Boyce et al.

[11] Patent Number: 5,616,819
[45] Date of Patent: Apr. 1, 1997

[54] PROCESS FOR PREPARING FLUORINATED ALIPHATIC COMPOUNDS

[75] Inventors: C. Bradford Boyce, Baton Rouge; Randolph K. Belter, Zachary, both of La.

[73] Assignee: LaRoche Industries Inc., Atlanta, Ga.

[21] Appl. No.: 519,779

[22] Filed: Aug. 28, 1995

[51] Int. Cl.$^6$ .................................................. C07C 17/08
[52] U.S. Cl. ........................ 570/167; 570/166; 570/168; 570/169
[58] Field of Search .................................. 570/167, 168, 570/169, 166

[56] References Cited

U.S. PATENT DOCUMENTS

| | | | |
|---|---|---|---|
| 5,202,509 | 4/1993 | Laviron et al. | 570/167 |
| 5,243,105 | 9/1993 | Scott et al. | 570/167 |
| 5,347,059 | 9/1994 | Pennedreau et al. | 570/167 |

*Primary Examiner*—Alan Siegel
*Attorney, Agent, or Firm*—Richard J. Hammond

[57] ABSTRACT

A process is disclosed for the preparation of a fluorinated aliphatic olefin having the formula $$CH_aF_{3-a}-CH_2-CH_bF_{3-b}$$

wherein a is 0 or the integer 1 or 2 and b is 0 or the integer 1, 2 or 3.

In the first step of the process, a chlorinated olefinic hydrocarbon of the formula $$CH_cCl_{2-c}=CH-CH_dCl_{3-d}$$

wherein c is 0 or the integer 1 and d is 0 or the integer 1 or 2 is reacted with anhydrous hydrogen fluoride for a period of time and at a temperature sufficient to form a chlorofluoro olefin of the formula $$CH_eCl_{2-e}=CH-CH_fF_{3-f}$$

wherein e is 0 or the integer 1 and f is 0 or the integer 1 or 2.

The chlorofluoro olefin produced in the first step is then reacted with anhydrous hydrogen fluoride in a second reaction. This second reaction is catalyzed with at least one compound that is a metal oxide or metal halide. Mixtures of said metal oxides, metal halides and metal oxides with metal halides may also be used. The metallic part of such compound is arsenic, antimony, tin, boron or is selected from a metal in Group IVb, Vb. VIb. VIIb or VIIIb of the Periodic Table of the Elements.

The desired fluorinated aliphatic hydrocarbon is subsequently separated and recovered.

The process is particularly suitable for the preparation of 1,1,1,3,3-pentafluoropropane.

13 Claims, No Drawings

PROCESS FOR PREPARING FLUORINATED ALIPHATIC COMPOUNDS

FIELD OF THE INVENTION

This invention relates to a process for preparing aliphatic compounds substituted with multiple fluorine atoms. In particular, this invention relates to the discovery that highly fluorinated aliphatic compounds can be prepared in high yield by a two step process comprising an uncatalyzed halogen/fluorine exchange of an chlorinated olefin followed by a catalyzed hydrofluorination and halogen/fluorine exchange of the resulting chlorofluoro intermediate.

BACKGROUND OF THE INVENTION

The replacement of chlorofluorocarbons (CFC's) widely used in refrigerant compositions, propellants and cooling fluids as well as blowing agents, solvents and rinse agents with environmentally acceptable alternatives has produced an abundance of compounds meeting one or more of these needs. The most acceptable replacement compounds are those having little or no chlorine, since it is generally accepted that chlorinated aliphatic hydrocarbons lead to unacceptably reactive chlorine-containing radicals when present in the upper atmosphere. These radicals are thought to react with the ozone in the stratosphere depleting it to dangerously low levels.

One of the more promising alternatives to CFC's are the aliphatic compounds where chlorine has been replaced with fluorine. These materials are known as hydrofluorocarbons (HFC's). Typical HFC's have atmospheric lifetimes and global warming potentials that are a fraction of their chlorinated analogs. However, many of their other physical properties (low flammability and toxicity, sufficient volatility, etc.) are identical or similar to the CFC's. Accordingly, they are attractive replacements for the chlorinated molecules.

In processes for preparing HFC's, a usual starting material is the chlorinated analog of the desired fluorinated compound. Thus, U.S. Pat. No. 2,787,646 discloses that $SbF_3Cl_2$ and/or $SbF_3$ are useful for converting compounds of the formula $CMZ_2CX=CHY$, for example 3,3,3-trichloroprop-1-ene or 1,1,3-trichloroprop-1-ene to compounds of the formula $CF_3CX=CHY$, for example 3,3,3-trifluoroprop-1-ene.

U.S. Pat. No. 2,549,580 discloses the conversion of 1,1-dichloroprop-1-ene to 1,1,1-trifluoropropane by means of hydrogen fluoride at 120° C. and 800 psi pressure.

The preparation of 1-chloro-1,1,3,3,3-pentafluoropropane and of 1,1,1,3,3,3-hexafluoropropane from 1,1,1,3,3,3-hexachloropropane in the liquid phase is described in EPO Publication No. 0 522 639 A1. While the preferred catalyst for the reaction is noted to be $SbCl_5$, other catalysts disclosed are those metal chlorides, fluorides, and chloride fluorides of Group IIIa, IVa, IVb, Va, Vb and VIb of The Periodic Table of the Elements.

Compounds such as 1,1,1,3,3,3-hexafluoropropane are prepared by the coupling of two chlorine containing reactants, i.e., 1,1,1-trichloro-2,2,2-trifluoroethane and dichlorodifluoromethane, in the presence of hydrogen and a first catalyst to form an olefin, i.e., 1,1,1,3,3-pentafluoro-2-chloroprop-2-ene and then hydrogenating the olefin in the presence of a second catalyst. See WO 95/05353.

SUMMARY

The process of the present invention to prepare a fluorinated aliphatic hydrocarbon utilizes a chlorinated olefinic hydrocarbon as the starting material. The olefin has the formula

$$CH_cCl_{2-c}=CH-CH_dCl_{3-d}$$

wherein c is 0 or the integer 1 and d is 0 or the integer 1 or 2. In the first step of this process, the olefin is reacted with anhydrous hydrogen fluoride (HF) for a time and at a temperature sufficient to form a second olefin where some of the chlorine atoms in the starting material have been replaced with fluorine. The second olefin has the formula

$$CH_eCl_{2-e}=CH-CH_fF_{3-f}$$

wherein e is 0 or the integer 1 and f is 0 or the integer 1 or 2. This second olefin is then reacted with anhydrous HF to form the desired fluorinated aliphatic hydrocarbon, i.e., a compound of the formula

$$CH_aF_{3-a}-CH_2-CH_bF_{3-b}.$$

This reaction may be catalyzed with a catalytically effective amount of at least one metal oxide or at least one metal halide. Mixtures of these metal oxides, metal halides or metal oxides with metal halides may also be advantageously used.

DESCRIPTION OF THE PREFERRED EMBODIMENTS

The process of the present invention is particularly useful for producing highly fluorinated aliphatic compounds that are not easily prepared in typical fluorine-for-chlorine substitution reactions.

Thus, for example, in the catalyzed reaction of 1,1,1,3,3-pentachloropropane with hydrogen fluoride, fluorine substitution for chlorine is accompanied by much tar and byproducts so that the pentafluoro compound is not formed in commercially acceptable yields.

Similarly, polychloro olefins such as 1,1,3,3-tetrachloroprop-1-ene with anhydrous hydrogen fluoride and a typical catalyst fail to yield the desired pentafluoropropane in acceptable yields due to extensive tarry residue formation.

The process of the present invention overcomes these and other disadvantages by preparing in a first step a partially fluorinated, chloroolefin of the formula

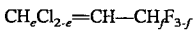

$$CH_eCl_{2-e}=CH-CH_fF_{3-f}$$

wherein e is 0 or the integer 1 and f is 0 or the integer 1 or 2 from the reaction of a polychloro compound of the formula

$$CH_cCl_{2-c}=CH-CH_dCl_{3-d}$$

wherein c is 0 or the integer 1 and d is 0 or the integer 1 or 2 with anhydrous hydrogen fluoride. The reaction is carried out for a time and at a temperature sufficient to produce the partially fluorinated, chloro olefin, also referred to herein as a "chlorofluoro-olefin".

In the above-disclosed first step, it is preferred that the polychloro compound is one where c is 0 or the integer 1 and d is the integer 1 or 2. Most preferably, c is 0 and d is 1, or c is 1 and d is 0.

At least three moles of anhydrous hydrogen fluoride are required to produce the partially fluorinated, chloro-olefin. However, an excess of hydrogen fluoride, preferably from about 2 to about 10 times the stoichiometric requirements are typically used in this reaction to facilitate the formation of the fluorochloro-olefin.

The reaction can be carried out as a batch or continuous process. In the batch mode, the polychloro olefin starting material may be added to the reaction vessel first. Order of addition is not critical. Hydrogen fluoride is then introduced and the reaction vessel heated, with agitation, to a temperature and over a period of time sufficient to produce the desired partially fluorinated olefin, i.e., a temperature of from about 70° C. to about 120° C., preferably about 80° C. to about 100° C., for from about 15 minutes to about 24 hours. The pressure during this reaction step is maintained at 200–230 psia by means of a back pressure regulator and the HCl generated is vented through a reflux condenser. HF and products carried along with the waste HCl are condensed and returned to the reactor. Accordingly, the reaction is run in the liquid phase for convenience although the reaction may be run in the vapor phase over an appropriate surface such as aluminum fluoride. This procedure is a conventional one and well known in the fluorine chemistry art.

At the conclusion of the reaction, the reaction vessel is cooled, typically to about 50° C. and the partially fluorinated chloro-olefin and excess HF is then flash distilled. The resulting mixture is used "as is" without futher purification for the second step of the process of the present invention.

The continuous mode requires continuous mixing at a flow rate and temperature sufficient to assure the contact times at the temperature range noted above. Continuous removal of the fluorochloro product and the by-product gases with HF is, of course, required.

As noted herein, the chlorofluoro olefin collected from the first reaction step is typically used without futher purification in the second step of the process of the present invention. This second step may also require additional anhydrous hydrogen fluoride in the second reaction vessel which, in this step, contains a catalyst. As in the first step, the reaction which is also carried out in the liquid phase with removal of HCl or under autogenous pressure, can be in the continuous or in a batch mode. The catalyst is typically introduced into the reaction vessel prior to the partially fluorinated, chloro olefin and HF.

A variety of catalysts (or mixtures of catalysts) are useful in carrying out the second step of the reaction of the present invention. To a large extent, many of these catalysts are equivalent and the choice depends on cost, availability and solubility in the reaction mass. The catalysts are metal halides or oxides or mixtures of such compounds, the metals being selected from the group consisting of arsenic, antimony, tin, boron, and from metals of Group IVb, Vb, VIb, VIIb, or VIIIb of the Periodic Table of the Elements. Preferably the metal compound is a chloride or fluoride, most preferably a fluoride. It is preferably antimony, arsenic, tin, bismuth or from Group IVb or VIIIb of the Periodic Table of the Elements. Preferably the catalyst is selected from the fluorides of antimony, tin, titanium and mixtures thereof. Most preferably, the catalyst is a mixture of antimony (V) and titanium (IV). While molar ratios of antimony to titanium of about 3 to about 5 may be used, it is especially preferred to use a molar ratio of antimony (V) to titanium (IV) in a 4 to 1.

The amount of catalyst used in the reaction is sufficient to catalyze the reaction. It is at least 1 mmol and preferably about 10 to about 200 mmol, per mole of partially fluorinated, chloro-olefin used in batch operation. At very low concentrations of catalyst, the reaction of the second step may be unacceptably slow. A very high concentration of catalyst may be wasteful due to the fact that the solubility limit may have been reached in the reaction mass. Consequently, the most preferred amount of catalyst is from about 10 to about 50 mmol, per mole of chlorofluoro olefin.

The second step of the reaction is conducted for a time and at a temperature sufficient to form the desired fluorinated aliphatic hydrocarbon. This is typically in the range of from about 25° C. to about 150° C. for about 15 minutes to about 24 hours. Preferably the reaction temperature is from about 75° C. to about 175° C., most preferably 80° C. to about 100° C. for from about 45 minutes to about 6 hours. Higher temperatures (above 200° C.) are required for a vapor phase reaction.

During the second step of the reaction, a reaction mass is produced that is essentially a mixture of the desired product (the fluorinated aliphatic hydrocarbon), hydrogen fluoride, catalyst and very small amounts of unreacted starting material from step i.) and from step ii.). The components of the mixture are not readily separated from the fluorinated aliphatic hydrocarbon end product by conventional methods.

For example, conventional distillation does not result in a separation of the end product from hydrogen fluoride because these materials have similar boiling points. Liquid/liquid phase separation is impractical as the two materials are miscible. The standard method for inducing phase separation (addition of an unreactive solvent that dissolves the fluorinated hydrocarbon, but not hydrogen fluoride) is not efficient.

It has now been discovered that the fluorinated aliphatic hydrocarbon can easily be separated from a hydrogen fluoride mixture, such exemplified by the reaction mixture formed in step ii.) by adding to such mixture an organic or inorganic salt that preferentially dissolves in the hydrogen fluoride and causes an insoluble liquid phase substantially enriched in the fluorinated aliphatic hydrocarbon to separate.

In order to be effective in this separation process, the organic or inorganic salt must be unreactive to the components of the reaction mixture, sufficiently soluble in hydrogen fluoride, e.g., the reaction mixture, to cause the phase enriched with the fluorinated aliphatic hydrocarbon to separate out as an easily recovered separate phase, relatively insoluble in the fluorinated hydrocarbon end product and readily separated from the resulting residual mixture after the fluorinated aliphatic hydrocarbon has been separated.

The organic salts useful to effect such separation include ammonium and lower alkyl ammonium fluorides, e.g., ammonium fluoride and mono, di, tri or tetra $C_1$ to $C_3$ linear or branched alkyl ammonium fluorides. Preferably, such salts include ammonium fluoride, mono and dimethylammonium fluoride and mono and diethylammonium fluoride. Particularly useful is ammonium fluoride.

The inorganic salts useful to effect such separation process include the fluorides and the bifluorides (sometimes called "acid fluorides") of the metals of Group Ia of the Periodic Table of the Elements. Preferably the fluorides and acid fluorides of lithium, sodium and potassium are used in this process. Most preferred are the fluorides of sodium and potassium.

The quantity of organic or inorganic salt added to the reaction mass is directly proportional to the amount of fluorinated aliphatic hydrocarbon that appears in the enriched, liquid separate phase. Thus, as little as 0.01 mole of salt per mole of hydrogen fluoride (calculated) is sufficient to result in the separation of a second liquid phase. If more than 0.25 mole of salt is used per mole of hydrogen fluoride (calculated), then crystallization of the reaction mixture may occur, (a crystalline complex is formed between the salt and hydrogen fluoride) interfering with separation of the desired product. Preferably the salt is used in an amount of 0.02 to about 0.20 mole per mole of hydrogen fluoride (calculated), most preferably about 0.05 to about 0.10 mole.

In the following examples, specific embodiments of the process of the present invention are disclosed. These are not included as limitations on the process but are for the purposes of illustration only. Unless indicated otherwise, temperatures are degrees Centigrade.

EXAMPLES

Example 1

Preparation of 1,1,1,3,3-tetrafluoropropane from 1,1,3,3-tetrachloropropene via 1-chloro-3,3,3-trifluoropropene.

i.

(Uncatalyzed)

Preparation of 1-chloro-3,3,3-trifluoropropene from 1,1,3,3-tetrachloropropene

A 450 ml hastelloy autoclave, fitted with a condenser and back pressure regulator, was evacuated and cooled in a dry ice/acetone bath. The condenser was maintained at 0° C. The reactor was charged with 120 g (6 mole) of anhydrous HF. The reactor was then charged with 180 g (1 mole) of 1,1,3,3-tetrachloropropene. The reactor was heated to 80° C. and the pressure maintained at 200 p.s.i. by venting HCl through the pressure regulator. When HCl evolution ceased, the reactor was cooled to 50° C. and discharged through a KOH scrubber and into a separatory funnel full of ice. The product was decanted as the more dense layer into a chilled bottle.

An average isolated yield of 107 g (80%) was achieved for each of 4 consecutive runs. For each run, approximately 19 g of oligomeric material was recovered from the reactor.

ii.

(Catalyzed)

Preparation of 1-chloro-3,3,3-trifluoropropene from 1,1,3,3-tetrachloropropene (SbCl$_5$ catalyzed)
A 450 ml hastelloy autoclave, fitted with a condenser and pressure regulator, was evacuated and cooled in a dry ice/acetone bath. The condenser was maintained at 0° C. The reactor was charged with 3 g (0.01 mole) of SbCl$_5$ and 136 g (6.8 mole) of HF. The reactor was heated to 90° C. for 1 hour. The reactor was then cooled to 20° C. and the pressure of HCl was released. The reactor was then cooled in a dry ice/acetone bath and charged with 152 g (0.84 mole) of 1,1,3,3-tetrachloropropene. The reactor was maintained at 80° C. and the pressure maintained at 200 p.s.i. by venting HCl through the pressure regulator. When HCl evolution ceased, the reactor was cooled to 50° C. and discharged through a KOH scrubber and into a separatory funnel full of ice. The product was decanted as the more dense layer into a chilled bottle.

A total of 3 g (2.6%) of 1-chloro-3,3,3-trifluoro-propene was isolated. After washing, 109 g of oligomeric material was recovered from the reactor.

Similar results were obtained using fluorosulfonic acid (HOSO$_3$F) or SnCl$_4$ instead of SbCl$_5$.

iii.

(Sulfolane Solvent)

Preparation of 1-chloro-3,3,3-trifluoropropene from 1,1,3,3-tetrachloropropene

A 450 ml hastelloy autoclave, fitted with a condenser and pressure regulator, was evacuated and cooled in a dry ice/acetone bath. The condenser was maintained at 0° C. The reactor was charged with 75 ml tetramethylene sulfone (Sulfolane). The reactor was then cooled in a dry ice/acetone bath and charged with 134 g (6.7 mole) of HF and 180 g (1.0 mole) of 1,1,3,3-tetrachloropropene. The reactor was heated to 100° C. and the pressure maintained at 230 p.s.i. by venting HCl through the back pressure regulator. When HCl evolution ceased, the reactor was cooled to 70° C. and discharged through a KOH scrubber and into a separatory funnel full of ice. The product was decanted as the more dense layer into a chilled bottle.

An average isolated yield of 115 g (86%) was achieved for each of 4 consecutive runs. After washing, 2.3 g of oligomeric material was recovered from the reactor in each run.

Example 1b i.

(Catalyzed)

Preparation of 1,1,1,3,3-pentafluoropropane from 1-chloro-3,3,3-trifluoropropene (SbCl$_5$ catalyzed)
A 300 ml hastelloy autoclave was charged with 35 g (0.12 mole) of SbCl$_5$ and 48 g (2.4 mole) of HF. The reactor was heated to 80° C. for 1 hour. The reactor was then cooled to 20° C. and the pressure of HCl was released. The reactor was then cooled in a dry ice/acetone bath and charged with 68 g (3.4 mole) of HF and 140 g (1.04 mole) of 1-chloro-3,3,3-trifluoropropene. The reactor was heated to 80° C. After an initial exotherm and a subsequent pressure increase, the reactor was cooled to 50° C. and discharged through a KOH scrubber and into a separatory funnel full of ice. The product was decanted as the more dense layer into a chilled bottle.

An average of 112 g (76%) of 1,1,1,3,3-pentafluoropropane (71% purity) was isolated for each of 2 consecutive runs after which the catalyst appeared to be inactive. 4 g of oligomers were observed on this catalyst.

ii.

(Catalyzed)

Preparation of 1,1,1,3,3-pentafluoropropane from 1-chloro-3,3,3-trifluoropropene (SbCl$_5$/TiCl$_4$ catalyzed)
A 300 ml hastelloy autoclave was charged with 45 g (0.15 mole) of SbCl$_5$, 7 g (0.04 mole) TiCl$_4$ and 24 g (1.2 mole) of anhydrous HF. The reactor was heated to 90° C. for 1 hour. The reactor was then cooled to 20° C. and the pressure of HCl was released. The reactor was then cooled in a dry ice/acetone bath and charged with 60 g (3.0 mole) of HF and 134 g (1.0 mole) of 1-chloro-3,3,3-trifluoropropene. The reactor was heated to 90° C. After an initial exotherm and a subsequent pressure increase, the reactor was cooled to 50° C. and discharged through a KOH scrubber and into a separatory funnel full of ice. The product was decanted as the more dense layer into a chilled bottle.

An average of 131 g (95%) of 1,1,1,3,3-pentafluoropropane was isolated for each of 2 consecutive runs. No oligomeric material was observed in the reactor.

iii.

(Mixed Substrates)

Preparation of 1,1,1,3,3-pentafluoropropane from a Mixture of 1,1,3,3-tetrachloropropene and 1,3,3,3-tetrachloropropene A 450 ml hastelloy autoclave (reactor #1), fitted with a condenser and pressure regulator, was evacuated and cooled in a dry ice/acetone bath. The condenser was maintained at 0° C. The reactor was charged with 50 ml tetramethylene sulfone (Sulfolane). The reactor was then cooled in a dry ice/acetone bath and charged with 134 g (6.7 mole) of HF and 180 g (1.0 mole) of about a 4 to 1 mixture of 1,1,3,3 and 1,3,3,3-tetrachloropropene. The reactor was heated to 100° C. and the pressure maintained at 230 p.s.i. by venting HCl through the pressure regulator. When HCl evolution ceased, the reactor was cooled to 50° C.

A 300 ml hastelloy autoclave (reactor #2) was charged with 45 g (0.15 mole) of SbCl$_5$, 7 g (0.04 mole) TiCl$_4$ and 24 g (1.2 mole) of anhydrous HF. The reactor was heated to 90° C. for 1 hour. The reactor was then cooled to 20° C. and the pressure of HCl was released. The reactor was then cooled in a dry ice/acetone bath. The 300 ml reactor was charged directly with the contents of the 450 ml reactor (~204 g). Any weight deficit was made up with anhydrous HF. The reactor was heated to 90° C. After an initial exotherm and a subsequent pressure increase, the reactor was cooled to 50° C. and discharged through a KOH scrubber and into a separatory funnel full of ice. The product was decanted as the more dense layer into a chilled bottle.

An average of 126 g (85%) of 1,1,1,3,3-pentafluoropropane (75% purity) was isolated for each of 8 consecutive runs. The remainder was 1-chloro-1,3,3,3-tetrafluoropropane and 1,1-dichloro-3,3,3-trifluoropropane (so-called underfluorinated materials).

Reactor #1 contained a total of 45 g of oligomers after all 8 runs. Reactor #2 showed no evidence of tars.

Comparative Example

Reaction of Underfluorinated Materials

A 300 ml hastelloy autoclave, fitted with a condenser and pressure regulator, was charged with 45 g (0.15 mole) of SbCl$_5$, 7 g (0.04 mole) TiCl$_4$ and 48 g (2.4 mole) of anhydrous HF. The reactor was heated to 90° C. for 1 hour. The reactor was then cooled to 20° C. and the pressure of HCl was released. The reactor was then cooled in a dry ice/acetone bath and charged with 136 g (6.8 mole) of anhydrous HF and 220 g (1.56 mole) of a mixture of 48% 1,1,1,3,3-pentafluoropropane, 32% 1-chloro-1,3,3,3-tetrafluoropropane and 20% 1,1-dichloro-3,3,3-trifluoropropane. The condenser was maintained at 0° C. The reactor was heated to 90° C. and the pressure maintained at 250 p.s.i. by venting HCl through the pressure regulator. When HCl evolution ceased, the reactor was cooled to 60° C. and discharged through a KOH scrubber and into a separatory funnel full of ice. The product was decanted as the more dense layer into a chilled bottle.

An average of 200 g (93%) of 1,1,1,3,3-pentafluoropropane (98% purity) was isolated for each of 3 consecutive runs. No oligomeric material was observed in the reactor after all 3 runs.

Example 2

Separation of
1,1,1,3,3-Pentafluoropropane/Hydrofluoric Acid Mixture

A solution of 20 g of HF and 20 g of 1,1,1,3,3-pentafluoropropane was made in a Teflon separatory funnel. The solution was chilled in an ice bath and small amounts (see table below) of powdered sodium fluoride were slowly added. The funnel was shaken and allowed to settle. The lower organic layer was drawn-off, weighed and titrated with 0.5N sodium hydroxide solution using phenolphthalein as the indicator.

| Amount of NaF Added (grams) | 0 | 0.42 | 0.84 | 1.26 | 1.68 | 2.10 |
|---|---|---|---|---|---|---|
| Weight of Organic Layer (grams) | 0 | 0 | <1 | 7.10 | 10.60 | 13.40 |
| HF in Organic Layer (grams) | — | — | — | 0.72 | 0.73 | 0.35 |

We claim:

1. A process for preparing a fluorinated aliphatic hydrocarbon of the formula $$CH_aF_{3-a}—CH_2—CH_bF_{3-b}$$

wherein a is 0 or the integer 1 or 2 and b is 0 or the integer 1, 2 or 3, comprising i.) reacting a chlorinated olefinic-hydrocarbon of the formula $$CH_cCl_{2-c}=CH—CH_dCl_{3-d}$$

wherein c is 0 or the integer 1 or 2, and d is 0 or the integer 1 or 2 with anhydrous hydrogen fluoride at a temperature and for a time sufficient to form a chlorofluoro olefin of the formula $$CH_eCl_{2-e}=CH—CH_fF_{3-f}$$

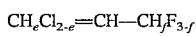

wherein e is 0 or the integer 1 or 2, and f is 0 or the integer 1 or 2 wherein said reacting is not catalyzed;

ii.) reacting said chlorofluoro olefin with anhydrous hydrogen fluoride and in the presence of a catalytically effective amount of at least one of a metal oxide or at least one of a metal halide or mixtures of said at least one metal oxide with at least one metal halide for a time and at a temperature sufficient to form a reaction mixture containing said fluorinated aliphatic hydrocarbon; and iii.) separating said fluorinated aliphatic hydrocarbon from said reaction mixture.

2. The process according to claim 1 wherein a, c and e are the integer 1 and b, d and f are the integer 0.

3. The process according to claim 1 wherein a, d and e are the integer 1 and b, c and f are the integer 0.

4. The process according to claim 1 wherein a and c are 0 and b and d are the integer 0.

5. The process according to claim 1 wherein steps i.) and ii.) are carried out in the liquid phase.

6. The process according to claim 1 wherein said temperature of step i.) is from about 50° C. to about 150° C.

7. The process according to claim 1 wherein said temperature of step ii.) is from about 25° C. to about 150° C.

8. The process according to claim 1 wherein said reacting of step ii.) is carried out in the presence of a metal oxide or of a metal halide.

9. The process according to claim 8 wherein the metal in said metal halide or oxide is selected from the group consisting of arsenic, antimony, tin, boron and a metal from Group IVb, Vb, VIb, VIIb, or VIIIb of the Periodic Table of the Elements.

10. The process according to claim 9 wherein the metal in said metal halide or oxide is antimony, arsenic, tin, bismuth or is one selected from the group of metals in Group IVb and VIIIb of the Periodic Table of the Elements.

11. The process according to claim 1 wherein the separation of step iii.) includes adding to said reaction mixture containing said fluorinated aliphatic hydrocarbon an organic or inorganic salt.

12. A process for preparing 1,1,1,3,3-pentafluoropropane which comprises i.) reacting a chloro olefin of the formula $$CH_cCl_{2-c}=CH-CH_dCl_{3-d}$$

wherein c and d are different and are 0 or the integer 1 with anhydrous hydrogen fluoride in the liquid phase and under autogenous pressure for a time and at a temperature sufficient to form a chlorofluoro olefin of the formula $$CH_eCl_{2-e}=CH-CH_fF_{3-f}$$

wherein e is 1 and f is 0 wherein said reacting is not catalyzed;

ii.) reacting said chlorofluoro olefin with anhydrous hydrogen fluoride and a catalytically effective amount of a halide or oxide of pentavalent antimony or a mixture of pentavalent antimony and tetravalent titanium for a time and at a temperature sufficient to form a reaction mixture containing said 1,1,1,3,3-pentafluoropropane; and iii.) separating said 1,1,1,3,3-pentafluoropropane from said reaction mixture by adding thereto a separation-causing amount of a compound selected from the group consisting of ammonium fluoride, sodium fluoride and potassium fluoride.

13. The process according to claim 12 wherein said mixture has a ratio of 4 parts antimony to 1 part titanium.

* * * * *